United States Patent [19]
Celada et al.

[11] Patent Number: 5,415,998
[45] Date of Patent: May 16, 1995

[54] ENZYME-CONTAINING QUATERNARY IMMUNOCOMPLEX HOMOGENEOUS ASSAY

[75] Inventors: Franco Celada, Milan, Italy; Gyorgy Görög, Budapest, Hungary

[73] Assignee: Applied Research Systems ARS Holding N.V., Curacao, Netherlands

[21] Appl. No.: 741,422
[22] PCT Filed: Dec. 22, 1989
[86] PCT No.: PCT/EP89/01612
§ 371 Date: Aug. 7, 1991
§ 102(e) Date: Aug. 7, 1991
[87] PCT Pub. No.: WO90/07714
PCT Pub. Date: Jul. 12, 1990

[30] Foreign Application Priority Data
Dec. 23, 1988 [IT] Italy .................. 48709A/88

[51] Int. Cl.[6] .............. G01N 33/535; G01N 33/542; G01N 33/577
[52] U.S. Cl. .................. 435/7.9; 435/967; 435/972; 435/975; 436/537; 436/548
[58] Field of Search ............. 435/7.1, 7.9, 7.92–7.95, 435/14, 21, 26, 28, 810, 962, 963, 964, 967, 972, 975, 7.71; 436/536, 537, 548; 424/88; 530/387.3, 388.26, 388.85, 388.9, 807

[56] References Cited
U.S. PATENT DOCUMENTS

| | | | |
|---|---|---|---|
| 4,687,735 | 8/1987 | DiNello et al. | 435/7.91 |
| 4,868,109 | 9/1989 | Lansdorp | 435/28 |
| 5,130,234 | 7/1992 | Hoshino et al. | 435/7.9 |
| 5,168,057 | 12/1992 | Oh et al. | 435/7.9 |

FOREIGN PATENT DOCUMENTS

| | | |
|---|---|---|
| 0034050 | 8/1981 | European Pat. Off. |
| 0096463 | 12/1983 | European Pat. Off. |
| 0119767 | 9/1984 | European Pat. Off. |
| 2167086 | 5/1986 | United Kingdom |
| 8504811 | 11/1985 | WIPO |

OTHER PUBLICATIONS

G. Gorog et al, "Use of bispecific hybrid antibodies for ... a homogeneous enzyme immunoassay", J of Immunol. Methods v 123 (1989) pp. 131–140.

N. Holmes et al, "Enhancement of Monoclonal Antibodies ..." J. of Biol. Methods v 258 No. 3 (1983) pp. 1580–1586.

W. Moyle et al, "A Circular Antibody Complex is Responsible for Increased Affinity ..." J. of Immunol. v. 131 No. 4 (1983) pp. 1900–1905.

K. Rubenstein et al, "'Homogeneous' Enzyme Immunoassay ..." Biochem Biophys Res Comm. v 47 No. 4 (1972) pp. 846–851.

I. Gibbons et al, "Homogeneous Enzyme Immunoassay ... Employing β-Galactosidase", Anal. Biochem. v 102 (1980) pp. 167–170.

Primary Examiner—David Saunders
Attorney, Agent, or Firm—Ostrolenk, Faber, Gerb & Soffen

[57] ABSTRACT

The invention concerns a method of homogeneous immunoassay of a ligand in a liquid test sample which comprises: a) incubating a mixture of (1) the liquid test sample; (1i) where the ligand under assay has only one epitope, a covalent conjugate of the ligand with any mono- or poly-epitope molecule having at least one epitope distinct from the epitope of the ligand; (2) a labile enzyme; (3) a first bispecific monoclonal antibody protecting the activity of the encyme through binding to a first epitope on the encyme and capable of binding the ligand under assay; and (4) a second bispecific monoclonal antibody capable of bonding said enzyme and a second distinct epitope on the ligand under assay or an epitope of the said covalent conjugate; whereby a quaternary immunocomplex is formed; b) after incubation, subjecting the mixture to conditions whereby any enzyme not present in such a quaternary immunocomplex is inactivated; and c) determining the amount of detectable encyme, the determination being related to the amount, if any, of ligand in the test sample. Kits for use in carrying out the method are also described.

14 Claims, 1 Drawing Sheet

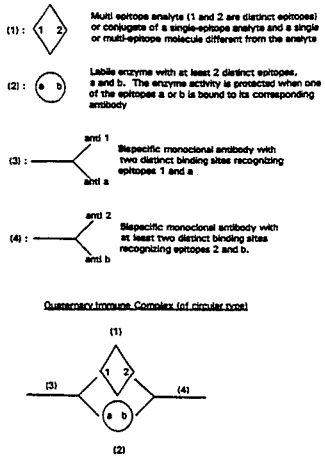

FIG.1

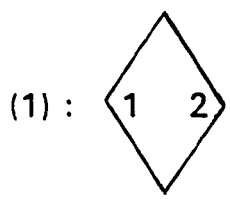

(1) : Multi epitope analyte (1 and 2 are distinct epitopes) or conjugate of a single-epitope analyte and a single or multi-epitope molecule different from the analyte

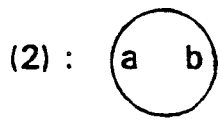

(2) : Labile enzyme with at least 2 distinct epitopes, a and b. The enzyme activity is protected when one of the epitopes a or b is bound to its corresponding antibody

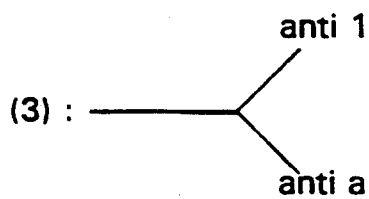

(3) : Bispecific monoclonal antibody with two distinct binding sites recognizing epitopes 1 and a

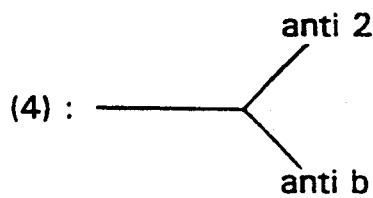

(4) : Bispecific monoclonal antibody with at least two distinct binding sites recognizing epitopes 2 and b.

Quaternary Immune Complex (of circular type)

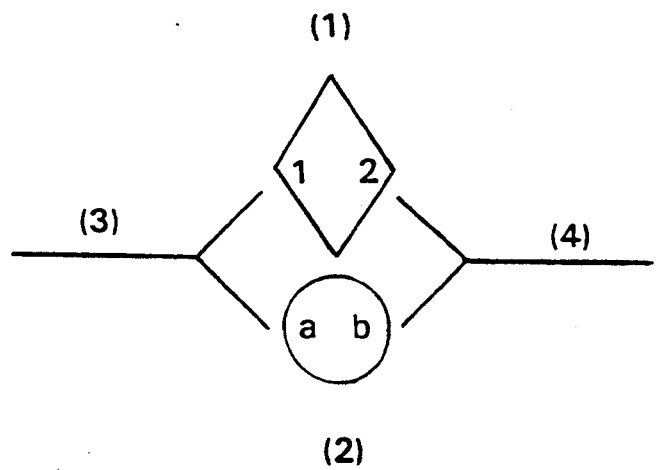

ENZYME-CONTAINING QUATERNARY IMMUNOCOMPLEX HOMOGENEOUS ASSAY

The present invention relates to an homogeneous immunoassay for determining the amount of a ligand in a liquid test sample and to kits for carrying out such assay.

In this specification the term ligand is to be taken to include any substance (e.g. antigen, antibodies), against which anti-ligands can be produced (e.g. antibodies and anti-antibodies) and accordingly includes within its scope haptens, which may have been rendered immunogenic for the purpose of producing antibodies.

Immunoassay techniques rely upon the formation of a complex between the antigen being assayed and antibodies which are added as part of the immunoassay procedure. Means are provided whereby the amount of antigen: antibody complex formation is detectable. There are several known methods of immunoassay employing antibodies which are labelled so as to be analytically identifiable. "Sandwich" or "two-site" techniques involve the formation of a complex between the antigen and two antibody reagents. A convenient method of detecting complex formation between an antigen in a liquid sample and two antibody reagents is to provide one labelled antibody reagent and an unlabelled reagent bound to a solid phase support so that the complex can readily be isolated. Where a radio-active label is employed this technique is known as immunoradiometric assay (IRMA).

One difficulty with this type of assay is the production of sufficiently pure labelled antibody. Whilst this can be done, it is a laborious procedure and hence relatively expensive. Recently, this problem has been reduced by the availability of monoclonal antibodies. Sandwich-type immunoassays involving the use of two monoclonal antibody reagents, a labelled soluble monoclonal antibody, and a monoclonal antibody which is bound to a water-insoluble solid phase, are described, for example in published European patent application N.0048357.

It is a feature of the technique described above that a significant incubation period is normally required to ensure that the reaction goes (so far as possible) to completion. This is due, at least in part, to the fact that the antigen in solution is required to react with antibody bound to a solid phase.

To avoid these problems, homogeneous immunoassays have been developed. Their use is however limited to the determination of drugs, hormones and plasma proteins. The homogeneous immunoassay known as EMIT (Biochem. Biophys. Res. Comun. 47:846,1972) has been applied successfully for the determination of small molecules like steroid hormones. In a modified EMIT the activity of the enzyme used as tracer is reduced when the conjugate enzyme-hapten (E-L) is bound to the antibody (AB). This seems to be due either to a reduced affinity of the substrate (S) towards the active site of the enzyme in presence of AB, or to a steric hindrance, or to a conformational modification of the enzyme. A further type of EMIT rests upon inhibition of the enzymatic tracer by the conjugated hapten. The tracer re-acquires its activity when the antibody (AB) against the hapten (L) binds the conjugate hapten-enzyme (E-L). A version of this method was developed for large antigen molecules (Anal. Biochem. 102: 167,1980) like IgG but its reported sensitivity seemed to be low. Fluorescence excitation transfer immunoassay (J. Biol. Chem. 251:4172, 1976) is based on the energy transfer between two fluorescent molecules, one on the antibody and the other on the antigen. Again, free analyte inhibits the complex formation between the antibody and the labelled antigen.

The enzyme channelling method (ECIA) (Anal. Biochem. 1056: 223, 1979) (Appl. Biochem. Biotechnol. 6,53–64 1981) makes use of an antibody and an antigen labelled with two different enzymes so that the product of the first enzyme reaction is the substrate of the second one. The overall reaction rate is greatly enhanced if the two enzymes are co-immobilised instead of being present separately in solution. Other techniques like the antigen-labelled fluorescence protection assay (Clin. Chem 25:1077, 1979) have also received attention.

Bispecific monoclonal antibodies (BSMAB) are antibodies in which the binding sites on the immunoglobulin molecule react with two distinct antigenic determinants. Therefore, BSMABs can simultaneously interact with different antigens.

Bispecific monoclonal antibodies have been produced by the chemical reassociation of monovalent fragments derived from two monoclonal antibodies. An alternative method of preparation involves the covalent attachment of whole monoclonal antibodies of different specificities using a heterobifunctional cross-linker. A third method for the preparation of bispecific monoclonal antibodies, cell fusion, was described in 1983 (Nature 305, 537–540, 1983; Human Immunol. 12:213, 1985; Science 229:81, 1981). Such antibodies have been utilized in solid enzyme immunoassays and histochemistry, replacing the antibody-enzyme conjugate of these methods. The use of bispecific antibodies in homogeneous immunoassay was also proposed (Biotech. Appl. and Research, Technomic, Lancaster, U.K., pages 401–409, 1986).

If one of the binding sites of a hybrid antibody binds to the epitope of a bivalent (or multivalent) analyte (ligand) while the other site binds to the epitope of a bivalent (or multivalent) enzyme, the presence of the analyte can, by allowing formation of circular complexes, enhance the binding of antibodies to enzyme.

Such an increase in binding efficiency of antibodies through formation of circular complexes has been reported by several authors (Trends Biochem 9:1, 1984).

One object of the present invention is to provide a method of homogeneous-immunoassay applicable to a wide range of ligands.

According to a first aspect of the present invention there is provided a method of homogeneous immunoassay of a ligand in a liquid test sample which comprises:
  a) incubating a mixture of
    (1) the liquid test sample;
    (1i) where the ligand under assay has only one epitope, a covalent conjugate of the ligand with any mono- or poly-epitope molecule having at least one epitope distinct from the epitope of the ligand;
    (2) a labile enzyme either present in at least a dimeric form or having at least two distinct epitopes;
    (3) a first bispecific monoclonal antibody in which one paratope is capable of protecting the activity of the enzyme through binding to a first epitope on the enzyme and the remaining paratope is capable of binding with a first epitope on the ligand under assay; and (4) a second bispecific monoclonal antibody in which either (i) in a case where the said enzyme is present in at least a dimeric form, the first paratope is functionally identical to the first paratope of the said first bispecific monoclonal antibody and is capable of binding to the enzyme similarly or (ii) in a case where the said enzyme has at least two distinct epitopes, the first paratope is capable of binding to a second epitope on the enzyme (not necessarily so as to protect the activity of the enzyme) and the second paratope is capable of binding to a second distinct epitope on the ligand under assay or (when the said ligand possesses only one epitope) to an epitope of the said covalent conjugate;

whereby a quaternary immunocomplex is formed;

b) after incubation, subjecting the liquid phase containing the mixture to conditions whereby any enzyme not present in such a quaternary immunocomplex is inactivated; and c) determining the amount of detectable enzyme, if any, which is bound as part of a quaternary immunocomplex, the determination being related to the amount, if any, of ligand in the test sample.

The term "labile enzyme" as used herein denotes any enzyme which may be inactivated by appropriate conditions employed in stage b).

The method is based on the ability of the antibody to protect the activity of an enzyme i.e. the effect of the antibody is to prevent the enzyme from losing its activity as a result of the conditions employed at stage b). The enzyme may retain its activity whilst it is bound as part of the quaternary complex so that the amount of enzyme bound as part of the complex may be determined without having to dissociate the complex first. Through the formation of quaternary (circular) complexes composed of bispecific antibodies, labile enzyme and the analyte to be determined, it is possible to correlate the amount of the enzymic activity present after denaturation to the amount of the ligand in the sample. This principle is possible because circular complexes formed are extremely stable. The enzyme molecule in the quaternary complexes is protected by the binding of the bispecific antibody against denaturation, whilst enzyme molecules not present as a quaternary immunocomplex are denatured by this treatment. In addition, any non-circular antibody-enzyme complexes tend to dissociate under the denaturising conditions and loss of enzyme activity results. This effect is increased where the affinity of the antibody for the enzyme is relatively low. Thus, upon the selection of monoclonal antibodies having a given affinity towards the enzyme it is possible to minimize any background activity. The quaternary complex may optionally comprise more than two bispecific monoclonal antibodies. Where this is the case, each antibody present in the complex is bound to both the ligand (or ligand-molecule conjugate) and the enzyme.

It will be understood that "distinct epitopes" may be functionally identical epitopes (but at different sites on a ligand, ligand-molecule conjugate or enzyme) or the epitopes may be functionally different.

When the ligand has only one epitope a suitable conjugate of the ligand and any mono- or poly-epitope molecule may be readily prepared in conventional manner. According to a preferred embodiment of the invention the labile enzyme is a thermo-labile enzyme. Thermo-labile enzymes are enzymes whose activity is affected by temperature. Inactivation of any free thermo-labile enzyme is carried out by heating. Thus, for example, a particularly suitable type of thermo-labile enzyme is the enzyme beta-galactosidase which undergoes heat denaturation at 62° C. resulting in enzyme inactivation. Suitable monoclonal antibodies protecting the enzyme beta-galactosidase from heat denaturation at 62° C. are described in Eur. J. Immunolog. 1978, 9:688–692 and P.N.A.S., USA 78:2478, 1981.

It would be readily apparent to the skilled man how to calibrate an assay in accordance with the invention.

The invention further provides an immunoassay kit for use in carrying out the foregoing methods.

According to a further aspect of the invention there is provided a kit for use in carrying out a method as described above, said kit comprising:

(i) a labile enzyme;
(ii) a first bispecific monoclonal antibody; and
(iii) a second bispecific monoclonal antibody, all as described above.

The kit may optionally further comprise a covalent conjugate of the ligand with any mono- or poly-epitope molecule having at least one epitope distinct from the ligand.

Optionally, the above kits may further comprise a calibrated reference solution.

A major advantage of the methods and kits of the present invention is that separation of the bound and free labelled reagent is eliminated. Moreover it allows the extension of homogeneous immunoassay to polyvalent ligands.

The ligand may be an antibody and in this case the first and second bispecific monoclonal antibodies are prepared starting from anti-antibodies.

When the ligand is a substance capable of binding specifically to an antibody, e.g. an antigen, then the bispecific monoclonal antibody may be a typical bispecific monoclonal antibody, i.e. prepared starting from monoclonal antibodies.

The method of the invention has very broad applicability, but in particular may be used to assay: hormones, including peptide hormones (e.g. thyroid stimulating hormone (TSH) luteninizing hormone (LH), human chorionic gonadotropin, hCG), follicle stimulating hormone (FSH), insulin and prolactin) or non-peptide hormones (e.g. steroids hormones such as cortisol, estradiol, progestrone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxin, vitamins, proteins, viruses such as influenza, para-influenza, adeno-, pefatitin, respiratory and AIDS viruses, or microorganisms. In a specific embodiment we have used it to determine carcinoembryonic antigen (CEA).

The binding of D6C9, a monoclonal antibody described in P.N.A.S., USA, 78:2478, 1981, protects E. coli Beta-galactosidase (GZ) from thermal denaturation. GZ, being a tetrameric enzyme, is multivalent with respect to the epitope critical for thermal denaturation.

The carcinoembryonal antigen (CEA) is monomeric. By taking advantage of the presence of two different epitopes (CEA-1 and CEA-2) an assay for CEA has been devised through the combined use of two sets of hybrid antibodies. Each hybrid antibody has a D6C9 anti-GZ binding site, while the other binding site is directed against the CEA-1 epitope or against the CEA-2 epitope.

The following preferred specific embodiments illustrate the invention by way of example only.

FIG. 1 illustrates schematically a quaternary immune complex formed in a method in accordance with the invention.

In the following example, all temperatures are set forth in degrees Celsius.

EXAMPLE

Immunoassay for CEA

1. Preparation of carcinoembrionic antigen (CEA).

CEA was purified from a colorectal carcinoma by the method of Krupey et al. (Immunochemistry, 1972, Vol.9, pp. 617–622) modified by Sluyter et al. (Cancer Research 36, 1696–1704, May 1976).

2. Beta-galactosidase enzyme.

Beta-galactosidase, grade VI was purchased from Sigma. Enzyme activity was measured using o-nitrophenyl-beta-D-galactoside (ONPG, Sigma) as substrate.

3. Monoclonal antibodies (monospecific) against CEA.

Anti-CEA monoclonal antibodies were prepared according to the teaching of Kohler and Milstein (Nature 1975, 256, 495–7). Two monoclonal antibodies were selected using an ELISA in which CEA was coated to the solid phase. The two monoclonal antibodies were designated CEA-1 and CEA-2.

4. Monoclonal antibody (monospecific) against beta-galactosidase.

Beta-galactosidase from E. Coli is composed of four identical subunits.

Anti-beta-galactosidase monoclonal antibodies were prepared according to the technic of Kohler and Milstein (see above). The resulting anti-beta-galactosidase monoclonal antibodies were screened for protecting beta-galactosidase activity from heat denaturation as described by Celada, P.N.A.S., USA, 78:2478/1981.

One of the hybridomas producing a protective anti-beta-galactosidase monoclonal antibody was designated D6C9.

5. Preparation of the first (CEA-1 x D6C9) and of the second (CEA-2 x D6C9) bispecific monoclonal antibody.

The preparation of bispecific monoclonal antibodies was carried out as described by Parham (Human Immunol. 12:213, 1985). Measurable hybrid antibody activity in both combinations (CEA-1 x D6C9) and (CEA-2 x D6C9) was obtained. The 2 bispecific monoclonal antibodies were purified by ion exchange chromatography on Mono Q chromatographic resin (Pharmacia) using an FPLC (fast protein, peptide and polynucleotide liquid chromatography) apparatus (Pharmacia). Samples were applied in a pH 8.0 Tris-HCl buffer and the proteins were eluted with a 0–0.3M NaCl gradient.

6. Bispecific antibody assay.

Microtiter plates were coated with CEA (1 mcg/ml) in PBS and blocked with BSA 1% albumin. Hybrid antibody was incubated on the plate for 1 hr at 37° C. After washings, 1 μg/ml beta-galactosidase was added and incubated for 1 hr at 37° C. Excess beta-galactosidase was washed away and ONPG was added. Colour development at 37° C. occurred for one hour.

7. Homogeneous immunoassay.

100 μl of bispecific antibody preparations, 50 mcl beta-galactosidase (1 μg/ml) and 50 mcl CEA (concentrations 0–10 μg/ml, all in 1% human albumin-PBS), were incubated in microtiter plates at room temperature for 10 min. The plates were then transferred to a 62° C. water bath and incubated for 1 hr. After quick cooling in tap water, 50 μl ONPG (5 Mg/ml) was added and the reaction was stopped after 20–30 min. Optical density was measured at 405 nm.

Enzyme activity due to the quaternary immunocomplex showed an increase up to a CEA concentration of 75 ng/ml. Above this CEA concentration, enzyme activity decreased and reached 0 level at 600 ng/ml indicating that at high CEA concentration, the quaternary immunocomplex dissociates.

We claim:

1. A method of homogeneous immunoassay for a ligand in a liquid test sample which comprises:
   a) incubating a mixture of
      (1) the liquid test sample;
      (2) where the ligand has only one epitope, a covalent conjugate of the ligand with a mono- or poly-epitope molecule having at least one epitope distinct from the epitope of the ligand;
      (3) an enzyme either present in at least a dimeric form or having at least two distinct specific binding epitopes, wherein incorporation of the enzyme into a circular quaternary immunocomplex protects against loss of enzymatic activity under denaturing conditions;
      (4) a first bispecific monoclonal antibody which does not bind to or sterically inhibit said enzyme's active site and in which one paratope protects the activity of the enzyme through specific binding to a first epitope on the enzyme and the remaining paratope specifically binds a first epitope on the ligand; and
      (5) a second bispecific monoclonal antibody which does not bind to or sterically inhibit said enzyme's active site and in which either (i) in the case where the enzyme is present in at least a dimeric form, the first paratope is functionally identical to the first paratope of the first bispecific monoclonal antibody and specifically binds to the enzyme or (ii) in the case where the enzyme has at least two distinct epitopes, the first paratope specifically binds to a second epitope on the enzyme but not necessarily so as to protect the activity of the enzyme and the second paratope specifically binds to a second distinct epitope on the ligand or when the ligand possesses only one epitope to an epitope of the covalent conjugate;
   whereby said quaternary immunocomplex is formed;
   b) after incubation, subjecting the mixture to denaturing conditions under which any enzyme not incorporated into said quaternary immunocomplex substantially loses its enzymatic activity; and
   c) determining the amount of enzymatically active enzyme, the determination being related to the amount of ligand in the test sample.

2. The method as claimed in claim 1 wherein the enzyme is a thermo-labile enzyme.

3. The method as claimed in claim 2 wherein the thermo-labile enzyme is beta-galactosidase.

4. The method as claimed in claim 2 wherein the enzyme is inactivated by thermal denaturation at 62° C.

5. The method as claimed in claim 4 wherein the enzyme is β-galactosidase.

6. The method as claimed in claim 5 wherein the ligand to be determined is carcinoembryonic antigen.

7. The method as claimed in claim 1 wherein the ligand to be determined is carcinoembryonic antigen.

8. A kit containing reagents to be combined with a liquid test sample for determination of a ligand therein, the kit comprising at least one container containing the reagents and the reagents comprising (i) an enzyme which is in at least a dimeric form or having at least two distinct specific binding epitopes, wherein incorporation of the enzyme into a circular quaternary immunocomplex protects against loss of enzymatic activity under denaturing conditions;

(ii) a first biospecific monoclonal antibody which does not bind to or sterically inhibit said enzyme's active site and in which one paratope is capable of protecting the activity of the enzyme through specific binding to a first epitope on the enzyme and the remaining paratope is capable of specific binding with a first epitope on the ligand; and (iii) a second bispecific monoclonal antibody which does not bind to or sterically inhibit said enzyme's active site and in which either (a) in the case where the enzyme is present in at least a dimeric form, the first paratope is functionally identical to the first paratope of the first biospecific monoclonal antibody and is capable of specific binding to the enzyme or (b) in the case where the enzyme has at least two distinct epitopes, the first paratope is capable of specific binding to a second epitope on the enzyme but not necessarily so as to protect the activity of the enzyme and the second paratope is capable of specific binding to a second distinct epitope on the ligand.

9. The kit as claimed in claim 8, further comprising a covalent conjugate of the ligand with a mono- or poly-epitope molecule having at least one epitope distinct from the ligand.

10. The kit as claimed in claim 8, further comprising a calibrated reference solution.

11. The kit as claimed in claim 8 wherein the enzyme is a thermo-labile enzyme.

12. The kit as claimed in claim 11 wherein the thermo-labile enzyme is $\beta$-galactosidase.

13. The kit as claimed in claim 12, further comprising a covalent conjugate of the ligand with a mono- or poly-epitope molecule having at least one epitope distinct from the epitope of the ligand.

14. The kit as claimed in claim 13, further comprising a calibrated reference solution.

* * * * *